(12) United States Patent
Chopin et al.

(10) Patent No.: US 6,187,438 B1
(45) Date of Patent: Feb. 13, 2001

(54) TITANIUM DIOXIDE PARTICLES, METHOD FOR THEIR PREPARATION AND THEIR USE IN COSMETICS, VARNISH AND SURFACE COATING

(75) Inventors: Thierry Chopin, Saint-Leu la Foret; Dominique Dupuis, Deuil-la-Barre, both of (FR); Bernard Pacaud, Kobe (JP)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/214,624

(22) PCT Filed: Jul. 4, 1997

(86) PCT No.: PCT/FR97/01208

§ 371 Date: Jun. 23, 1999

§ 102(e) Date: Jun. 23, 1999

(87) PCT Pub. No.: WO98/01392

PCT Pub. Date: Jan. 15, 1998

(30) Foreign Application Priority Data

Jul. 8, 1996 (FR) .................................................. 96/08460
Sep. 27, 1996 (FR) ................................................ 96/11781

(51) Int. Cl.$^7$ ........................................................ B32B 5/16
(52) U.S. Cl. ........................... 428/403; 427/214; 427/215; 428/404; 428/405
(58) Field of Search ................................ 428/403, 404, 428/405; 427/212, 214, 215

(56) References Cited

U.S. PATENT DOCUMENTS

| | | | | |
|---|---|---|---|---|
| 3,615,204 | * | 10/1971 | Libera et al. .................... | 23/202 R |
| 3,617,217 | * | 11/1971 | Heywood ............................. | 23/202 |
| 3,919,388 | * | 11/1975 | Thompson et al. .................... | 423/69 |
| 4,183,768 | * | 1/1980 | Knapp et al. ........................ | 106/299 |
| 4,461,810 | | 7/1984 | Jacobson ............................ | 428/530 |
| 4,705,770 | * | 11/1987 | Cullo et al. ........................ | 502/242 |
| 4,737,194 | * | 4/1988 | Jacobson ............................ | 106/300 |
| 4,885,034 | * | 12/1989 | Kreth et al. ........................ | 106/449 |
| 4,923,682 | | 5/1990 | Roberts et al. ...................... | 423/611 |
| 4,927,464 | * | 5/1990 | Cowie ............................... | 106/436 |
| 5,215,580 | * | 6/1993 | Elfenthal et al. .................... | 106/441 |
| 5,330,953 | * | 7/1994 | Meina ............................... | 502/208 |
| 5,423,912 | * | 6/1995 | Sullivan et al. ..................... | 106/417 |
| 5,554,215 | * | 9/1996 | Simpson et al. ...................... | 106/436 |
| 5,565,025 | * | 10/1996 | Schraml-Marth ....................... | 106/417 |
| 5,630,995 | * | 5/1997 | Foulger et al. ...................... | 423/616 |
| 5,643,974 | * | 7/1997 | Simpson et al. ...................... | 523/334 |
| 5,688,439 | * | 11/1997 | Chopin et al. ....................... | 252/309 |
| 5,851,652 | * | 12/1998 | Jacobson et al. ..................... | 428/328 |
| 5,858,078 | * | 1/1999 | Andes et al. ........................ | 106/437 |
| 5,910,213 | * | 6/1999 | Ashdown et al. ...................... | 106/436 |
| 5,955,091 | * | 9/1999 | Hansenne ............................ | 424/401 |

FOREIGN PATENT DOCUMENTS

| | | |
|---|---|---|
| 43 02 896 | 8/1994 | (DE) . |
| 0 401 045 | 12/1990 | (EP) . |
| 2 115 394 | 9/1983 | (GB) . |
| 95 12638 | 5/1995 | (WO) . |

* cited by examiner

Primary Examiner—H. Thi Le
(74) Attorney, Agent, or Firm—Burns, Doane, Swecker & Mathis, L.L.P.

(57) ABSTRACT

The invention concerns titanium dioxide particles coated at least partially: with a first layer of at least a cerium and/or iron compound, and a second layer of at least a metal oxide, hydroxide or oxohydroxide, the said particles having a BET specific surface area of at least 70 m$^2$/g and a density of 2.5. The invention also concerns a method for preparing these particles and their use as anti-UV agent.

20 Claims, No Drawings

TITANIUM DIOXIDE PARTICLES, METHOD FOR THEIR PREPARATION AND THEIR USE IN COSMETICS, VARNISH AND SURFACE COATING

The present invention relates to novel anatase titanium dioxides particles exhibiting anti-UV properties which can be used in particular in cosmetic formulations, varnishes and transparent coverings.

It is known to use titanium dioxide as anti-UV agent in numerous applications, in particular in cosmetics, paint, plastics, and the like.

In these applications, the titanium dioxide is generally provided in the form of particles with a size of less than 100 nm as a dispersion in an aqueous or organic phase.

The problem resulting from the use of these dispersions of titanium dioxide particles arises from the fact that the latter are often unstable. To control their stability, it is known to add dispersing agents to them, generally organic polymers.

However, the addition of these dispersing agents is not a solution which is without its disadvantages. This is because, when the titanium dioxide dispersion is mixed with other products in order to prepare a cosmetic, paint or plastic formulation, this agent can exhibit behaviour incompatible with the application (stability, agglomeration, toxicity, and the like) or be incompatible with the other components of the formula.

In these applications, the need is thus felt to be able to have available dispersions of titanium dioxide particles which are stable without the addition of dispersing agent.

One aim of the present invention is thus to provide dispersions of titanium dioxide particles which are stable and which do not contain dispersing agent.

With this aim, the invention relates to titanium dioxide particles at least partially covered:
  with a first layer of at least one cerium and/or iron compound, and
  with a second layer of at least one metal oxide, hydroxide or hydroxide oxide, the said particles exhibiting a BET specific surface of at least 70 m$^2$/g and a relative density of the order of 2.5.

With this aim, the invention also relates to the process for the preparation of these particles in which the following stages are employed:
  at least one cerium and/or iron compound is precipitated at the surface of anatase titanium dioxide particles with a size of at most 100 nm exhibiting a BET specific surface of at least 200 m$^2$/g and a relative density of the order of 2.5, then
  at least one metal oxide, hydroxide or hydroxide oxide is precipitated at the surface of particles obtained.

Finally, the invention also relates to the use of these particles as anti-UV agent in cosmetic, paint, varnish or transparent covering formulations and in plastics; and more particularly to an anti-UV cosmetic composition and to an anti-UV transparent covering composition.

The dispersions of particles according to the invention in addition exhibit the advantage of being stable over a wide pH range without addition of dispersing agent.

They can also exhibited high solids contents, while remaining stable and exhibiting a low viscosity, in particular of less than 1000 mPa·s.

Moreover, it is observed that these dispersions retain the same dispersion index even when they have been mixed with the components of a formulation, for example a cosmetic formulation.

Other characteristics, details and advantages of the invention will become more clearly apparent on reading the description and examples which will follow.

The invention first of all relates to titanium dioxide particles at least partially covered:
  with a first layer of at least one cerium and/or iron compound, and
  with a second layer of at least one metal oxide, hydroxide or hydroxide oxide, the said particles exhibiting a BET specific surface of at least 70 m$^2$/g and a relative density of the order of 2.5.

The particles according to the invention are based on titanium dioxide with a largely anatase crystalline structure. "Largely" means that the level of anatase in the titanium dioxide particles of the coating is greater than 50% by mass. Preferably, the particles of the coating exhibit a level of anatase of greater than 80%. The degree of crystallization and the nature of the crystalline phase are measured by X-ray diffraction.

The mean diameter of these particles is at most 100 nm, preferably at least 25 nm, more preferably still between 50 and 70 nm. This diameter is measured by transmission electron microscopy (TEM).

The particles according to the invention exhibit a BET specific surface of at least 70 m$^2$/g, preferably of at least 100 m$^2$/g.

BET specific surface is understood to mean the specific surface determined by nitrogen adsorption in accordance with the ASTM standard D 3663-78 drawn up from the Brunauer-Emmett-Teller method described in the periodical "The Journal of the American [lacuna] Society", 60, 309 (1938). In order to measure the specific surface of the particles according to the invention, when they are provided in the form of a dispersion, it is essential to follow the measuring protocol, which consists in removing the liquid phase from the dispersion and then in drying the particles under vacuum at a temperature of 150° C. for at least 4 hours.

The particles according to the invention also exhibit a relative density of the order of 2.5. "Of the order" is understood to mean that the relative density is 2.5+/−0.2. Such a relative density value is low with respect to the conventional relative density of anatase titanium dioxide, which is 3.8. This relative density is measured by picnometry.

The particles according to the invention are at least partially covered with a first inorganic layer based on at least one cerium and/or iron compound. These compounds are precursors of cerium or iron oxide, that is to say that they can be thermally decomposed to cerium or iron oxide. They can generally be cerium or iron salts.

According to the invention, particles covered with a cerium compound are preferred. The best results as regards dispersion properties were obtained for the particles where the ratio by weight of the cerium compound or compounds to the titanium dioxide is at most 6% by weight, expressed as $CeO_2$.

This ratio can be optimized as a function of the size of the particles. Thus, it was observed that, for particles with a diameter of 25 nm, the optimum cerium content was 5.5% by weight, expressed as $CeO_2$, with respect to the titanium dioxide, likewise, for particles with a diameter of 45 nm, this content is 4.5%, for particles with a diameter of 60 nm, this content is 3% and, for particles with a diameter of 80 nm, this content is 2%.

These particles are also at least partially covered with a second layer based on at least one metal oxide, hydroxide or hydroxide oxide. The oxide is generally SiO$_2$, with regard to the metal hydroxide or hydroxide oxide, it can be chosen in particular from aluminium, zinc, titanium or tin hydroxides or hydroxide oxides, in the simple or mixed form. Mixed is understood to mean a metal compound based on at least two of the abovementioned elements (silicoaluminates, and the like).

In general, the ratio by weight of the metal oxide(s), hydroxide(s) or hydroxide oxide(s) to the titanium dioxide is at most 60% by weight. This ratio depends on the application for which the particles are intended. Preferably, when the particles are used in a cosmetic application, this ratio is at most 25%, more preferably still at most 20%.

These amounts of metal compounds, oxides, hydroxides or hydroxide oxides are measured on the dispersed particles by X-ray fluorescence.

According to the preferred form of the invention, the particles are at least partially covered with a first layer of a cerium compound and with a second layer based on silica and/or on an aluminium hydroxide or hydroxide oxide, in the simple or mixed form.

According to a preferred first alternative form, the particles are covered with a second layer based on silica and on aluminium hydroxide or hydroxide oxide in contents by weight of 15% of SiO$_2$ and 5% of Al$_2$O$_3$ with respect to the titanium dioxide.

According to a second, even more preferred, alternative form, the particles are covered with a second layer based solely on silica in a content by weight of 30% of SiO$_2$.

According to the preferred form of the invention, the particles are provided in the form of a dispersion.

This dispersion can exhibit a proportion of suspended solid (solids content) of between 10 and 60% by weight, preferably of at least 35%, more preferably still of at least 40%.

This dispersion generally exhibits a dispersion index of the particles in the liquid phase of at most 0.5. The dispersion index is determined by the formula:

$$I = \frac{\phi_{84} - \phi_{16}}{2\phi_{50}}$$

in which:
- $\phi_{84}$ is the diameter of the particles for which 84% of the particles have a diameter of less than $\phi_{84}$,
- $\phi_{16}$ is the diameter of the particles for which 16% of the particles have a diameter of less than $\phi_{16}$,
- $\phi_{50}$ is the mean diameter of the particles.

The diameters of use in the determination of the dispersion index are measured by centrifugal sedimentation of the particles of the dispersion, monitored by X-rays, using a Brookhaven type XDC device.

Such an index reflects the good dispersibility of the particles. In the case of aqueous dispersions, this index is obtained over a wide pH range which can vary from 5.5 to 10. The dispersions are stable and they retain this index value over time, despite the absence of dispersing agent.

According to a first form, this dispersion is in the aqueous phase.

This aqueous dispersion generally exhibits a conductivity of at most 3 msiemens.

The dispersion of particles according to the invention exhibiting a solids content of at least 35% have the advantage of being only slightly viscous, thus their viscosity is generally at most 1000 mPa·s.

According to a second form, this dispersion is in the organic phase. The latter is generally obtained from an aqueous dispersion and transfer of the particles into the organic phase.

For example, this transfer can be carried out by grafting a hydrophobic chain, for example a trialkoxysilane, to the surface of the particles in an aqueous dispersion. The dispersion of compatibilized particles is subsequently mixed with an organic medium, so as to cause the particles to migrate into the organic phase.

The organic dispersion can also be obtained by bringing an aqueous dispersion of titanium dioxide particles into contact with the desired organic solvent and then heating, so as to remove the water by distillation. The latter process can only be employed in the case where the chosen organic solvent exhibits a boiling temperature greater than that of water and is soluble in water.

Another process consists in mixing an aqueous dispersion with an organic medium comprising a cationic transfer agent, it being possible for the latter to be chosen, for example, from quaternary amines or quaternary ammonium salts, this process is disclosed more particularly in Patent GB-A-988,330.

Finally, these particles according to the invention can also be agglomerated and be provided in the form of a powder. The size of the agglomerates can be between 1 and 40 µm, measured by TEM.

Following an organic treatment, this powder can exhibit good redispersibility in an organic medium. This organic treatment can be carried out, for example, by atomization in the presence of a fatty acid, such as stearic acid, or of a metal salt of a fatty acid.

The invention also relates to the process for the preparation of these particles, which consists in employing the following stages:
- at least one cerium and/or iron compound is precipitated at the surface of anatase titanium dioxide particles with a size of at most 100 nm exhibiting a BET specific surface of at least 200 m$^2$/g and a relative density of the order of 2.5, then
- at least one metal oxide, hydroxide or hydroxide oxide is precipitated at the surface of particles obtained.

These precipitations can be carried out by:
- introducing, into a dispersion of particles of titanium dioxide exhibiting the characteristics defined hereinabove, precursors of the cerium and/or iron compounds, metal oxides, hydroxides or hydroxide oxides, generally in the form of aqueous salt solutions, then,
- modifying the pH in order to obtain the precipitation of these compounds, oxides, hydroxides or hydroxide oxides on the titanium dioxide particles.

This precipitation is generally carried out at a temperature of at least 50° C.

An important characteristic of the particles according to the invention is that they are not calcined, that is to say that they are not covered with cerium and/or iron oxides.

The cerium and/or iron compounds are generally cerium or iron salts or hydroxides. For cerium, they can be a cerium salt chosen from cerium acetate, cerium sulphate or cerium chloride.

Likewise, for the deposition of iron, they can be an iron chloride, sulphate or acetate.

According to a preferred form, this layer is obtained by precipitation of cerium acetate and/or of iron chloride.

The use of cerium nitrate or of iron nitrate is highly inadvisable, because the treatment obtained can have a tendency to result in a photoblueing effect of the formulation in which the titanium dioxide dispersion would be used.

The precipitation of the cerium and/or iron compounds is generally obtained for a pH of between 4 and 10.

It is possible to heat the dispersion of particles during this stage.

In the case of the precipitation of silica and of an aluminium hydroxide or hydroxide oxide, the precipitation can be carried out at acidic or basic pH. The pH is controlled by the addition of an acid, such as sulphuric acid, or by the simultaneous and/or alternating introduction of an alkaline compound of silicon and of an acidic compound of aluminium. In this case, the pH is preferably between 8 and 10.

The silica can be precipitated from a silicon salt, such as an alkaline silicate.

The aluminium hydroxide or hydroxide oxide can be precipitated from an aluminium salt, such as aluminium sulphate, sodium aluminate, basic aluminium chloride or aluminium diacetate hydroxide.

It is possible, after the precipitation, to recover and wash the particles obtained following the treatment, before redispersing them. This stage can be carried out by centrifuging and washing or, preferably, by washing by ultrafiltration. The pH of the aqueous wash liquor is advantageously of the order of 5.5. The particles are then redispersed in another liquid medium, so as to obtain a dispersion of titanium dioxide particles. This liquid medium can be acidic or basic, it is preferably a basic solution exhibiting a pH of the order of 8–9.

To obtain a powder of particles according to the invention, the dispersion resulting from the process is dried, generally at a temperature of less than 110° C.

The starting anatase titanium dioxide particles must exhibit a size of at most 100 nm, a BET specific surface of at least 200 m²/g and a relative density of the order of 2.5.

The starting particles are based on titanium dioxide with a mainly anatase crystalline structure, as defined above.

The mean diameter of these particles is at most 100 nm, preferably at least 25 nm, more preferably still between 50 and 70 nm. This diameter is measured by transmission electron microscopy (TEM).

The starting particles exhibit a BET specific surface of at least 200 m²/g, preferably of at least 250 m²/g.

This BET specific surface is measured in the same way as defined above.

The starting particles also exhibit a relative density of the order of 2.5. "of the order" is understood to mean that the relative density is 2.5+/−0.2. This relative density is given by the following formula:

$$\text{relative density} = \frac{1}{(1/\rho) + Vi}$$

in which:

$\rho$ is the relative density of the anatase, i.e. 3.8,

Vi is the volume contributed by the intraparticle pores; it is measured by the BJH method. Volume measured by the BJH method is understood to mean the volume measured from the Barrett-Joyner-Helenda method described in the article in the work Techniques de l'Ingénieur [Techniques of the Engineer] and entitled "Texture des solides poreux ou divisés" [Texture of porous or divided solids], p.3645–1 to 3645–13.

In order to measure the volume contributed by the intraparticle pores of the particles according to the invention, when they are provided in the form of a dispersion, it is essential to follow the measuring protocol which consists in removing the liquid phase from the dispersion and then in drying the particles under vacuum at a temperature of 150° C. for at least 4 hours.

Such particles can be obtained by hydrolysis of at least one titanium compound A in the presence of at least one compound B chosen from:

(i) the acids which exhibit:
either a carboxyl group and at least two hydroxyl and/or amine groups,
or at least two carboxyl groups and at least one hydroxyl and/or amine group, (ii) the organic phosphoric acids of following formulae:

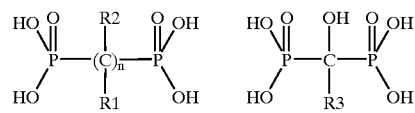

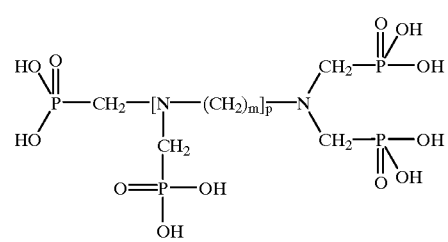

in which n and m are integers of between 1 and 6 and p is an integer of between 0 and 5; R1, R2 and R3, which are identical or different, representing a hydroxyl, amino, aralkyl, aryl or alkyl group or hydrogen, (iii) the compounds capable of releasing sulphate ions in acidic medium, (iv) the salts of the acids described above, and in the presence of anatase titanium dioxide seeds exhibiting a size of at most 8 nm, and in a weight ratio, expressed as ($TiO_2$ present in the seeds/titanium present before introduction of the seeds in the hydrolysis medium) expressed as $TiO_2$, of between 0.01% and 3%.

The starting solution, intended to be hydrolyzed, is preferably completely aqueous; it is optionally possible to add another solvent, for example an alcohol, provided that the titanium compound A and the compound B used are then substantially soluble in this mixture.

As regards the titanium compound A, use is generally made of a compound chosen from titanium halides, oxyhalides or alkoxides, sulphates and more particularly synthetic sulphates.

Synthetic sulphates are understood to mean titanyl sulphate solutions prepared by ion exchange from very pure titanium chloride solutions or by reaction of sulfuric acid with a titanium alkoxide.

The preparation is preferably carried out with titanium compounds of the titanium halide or oxyhalide type. The titanium halides or oxyhalides which are more particularly used in the present invention are titanium fluorides, chlorides, bromides and iodides (respectively oxyfluorides, oxychlorides, oxybromides and oxyiodides).

According to a particularly preferred form, the titanium compound is titanium oxychloride $TiOCl_2$.

The amount of titanium compound A present in the solution to be hydrolysed is not critical.

The initial solution additionally contains at least one compound B as defined above. Mention may be made, as non-limiting examples of compounds B coming within the scope of the present invention, of in particular:

hydroxypolycarboxylic acids and more particularly hydroxydi- or hydroxytricarboxylic acids, such as citric acid, maleic acid and tartaric acid, (polyhydroxy)monocarboxylic acids, such as, for example, glucoheptonic acid and gluconic acid, poly(hydroxycarboxylic) acids, such as, for example, tartaric acid, dicarboxylic monoacids and their corresponding amides, such as, for example, aspartic acid, asparagine and glutamic acid, hydroxylated or non-hydroxylated monocarboxylic amino acids, such as, for example, lysine, serine and threonine, aminotri(methylenephosphonate), ethylenediaminotetra(methylenephosphonate), triethylenetetraaminohexa(methylenephosphonate), tetraethylenepentaaminohepta(methylenephosphonate) or pentaethylenehexaaminoocta(methylenephosphonate), methylenediphosphonate, 1,1'-ethylenediphosphonate, 1,2-ethylenediphosphonate, 1,1'-propylenediphosphonate, 1,3-propylenediphosphonate, 1,6-hexamethylenediphosphonate, 2,4-dihydroxypentamethylene-2,4-diphosphonate, 2,5-dihydroxyhexamethylene-2,5-diphosphonate, 2,3-dihydroxybutylene-2,3-diphosphonate, 1-hydroxybenzyl-1,1'-diphosphonate, 1-aminoethylene-1-1'-diphosphonate, hydroxymethylenediphosphonate, 1-hydroxyethylene-1,1'-diphosphonate, 1-hydroxypropylene-1-1-1'-diphosphonate, 1-hydroxybutylene-1-1'-diphosphonate or 1-hydroxyhexamethylene-1,1'-diphosphonate.

As already indicated, it is also possible to use, as compound B, all the salts of the abovementioned acids. In particular, these salts are either alkali metal salts, more particularly sodium salts, or ammonium salts.

These compounds can also be chosen from sulphuric acid and ammonium or potassium sulphates, and the like.

The compounds B as defined above are preferably hydrocarbon-comprising compounds of aliphatic type. In this case, the length of the main hydrocarbon-comprising chain preferably does not exceed 15 carbon atoms and more preferably 10 carbon atoms. The preferred compound B is citric acid.

The amount of compound B is not critical. The molar concentration of the compound B with respect to that of the titanium compound A is generally between 0.2 and 10% and preferably between 1 and 5%.

Finally, the starting solution comprises titanium dioxide seeds used in a specific way.

Thus, the titanium dioxide seeds used in the present invention must first of all exhibit a size of less than 8 nm, measured by X-ray diffraction. Use is preferably made of titanium dioxide seeds exhibiting a size of between 3 and 5 nm.

Subsequently, the ratio by weight of the titanium dioxide present in the seeds to the titanium present in the hydrolysis medium before introduction of the seeds, that is to say contributed by the titanium compound A, and expressed as $TiO_2$ is between 0.01 and 3%. This ratio can preferably be between 0.05 and 1.5%. The bringing together of these two conditions with respect to the seeds (size and ratio by weight), in combination with the process as described above, makes it possible to precisely control the final size of the titanium dioxide particles, a level of seeds being associated with a particle size. It is thus possible to obtain particles for which the diameter varies between 25 and 100 nm.

Use is made of titanium dioxide seeds in the anatase form, so as to induce precipitation of the titanium dioxide in the anatase form. Generally, due to their small size, these seeds instead exist in the form of poorly crystallized anatase. The seeds are generally provided in the form of an aqueous suspension composed of titanium dioxide. They can generally be obtained in a known way by a process of neutralization of a titanium salt by a base.

The following stage consists in hydrolysing this starting solution by any means known to a person skilled in the art and generally by heating. In the latter case, the hydrolysis can preferably be carried out at a temperature greater than or equal to 70° C. It is also possible to operate, firstly, at a temperature below the boiling temperature of the medium and, then, to maintain the hydrolysis medium level at the boiling temperature.

Once hydrolysis has been carried out, the titanium dioxide particles obtained are recovered by separation of the precipitated solid from the mother liquors before being redispersed in a liquid medium so as to obtain a titanium dioxide dispersion. This liquid medium can be acidic or basic. It is preferably a basic solution, for example an aqueous sodium hydroxide solution. It is from this dispersion that the stage of precipitation of the metal oxides, hydroxides or hydroxide oxides will be carried out.

According to a specific alternative form, after the recovery of the particles obtained following the hydrolysis and before they are redispersed, the particles are neutralized and subjected to at least one washing operation. The particles can be recovered, for example by centrifuging the solution resulting from the hydrolysis; they are subsequently neutralized with a base, for example a sodium hydroxide or aqueous ammonia solution, they are then washed by redispersing them in an aqueous solution, and finally the particles are separated from the aqueous washing phase. After optionally one or more other washing operations of the same type, the particles are redispersed in an acidic or basic solution.

These particles generally exhibit a high degree of purity, compatible with an application in cosmetics.

Finally, the invention relates to the use of the particles described above as anti-UV agent. They can be used in particular as anti-UV agent in cosmetic formulations or coating formulations, such as varnishes, paints or transparent coverings, and in plastics.

Introduced into cosmetic formulations, these titanium dioxide dispersions or powders make it possible to obtain an SPF (Sun Protection Factor) number of at least 20.

Moreover, the formulations obtained are photostable, that is to say that they do not exhibit blueing after exposure to UV according to the test defined in the examples.

They are particularly stable on storage and it may be observed that the titanium dioxide particles retains their dispersion index in the formulation.

The invention relates to anti-UV cosmetic compositions comprising particles as described above in an amount such that the titanium dioxide content in the said compositions is at least 1%, preferably at most 25%, by weight and more preferably still between 2 and 10% by weight.

It is possible to introduce into the cosmetic compositions particles exhibiting different particle sizes.

The compositions forming the subject-matter of the invention can be formulated as a large number of types of products, such as anti-sun products of gel, lotion, oil or cream type and more generally make-up products, self-tanning agents, care products, hairs, total blocks for the lips and many other compositions of the same type.

The term cosmetic composition or formulation is understood to mean all cosmetic products or preparations, such as those described in Appendix I ("Illustrative list by category of cosmetic products") of European Directive No. 76/768/EEC of Jul. 27, 1976, known as the cosmetic directive.

The cosmetic compositions forming the subject-matter of the invention can involve a vehicle, or a mixture of several vehicles, which act as diluent, dispersant or support for the other constituents of the composition and make possible their distribution when the composition is spread over the skin or hair.

The vehicles other than water can be liquid or solid emollients, solvents, humectants, thickeners or powders. The following types of vehicles can be used, for example, alone or as a mixture:

emollients, such as stearyl alcohol, glyceryl monoricinoleate, oleyl alcohol, cetyl alcohol, isopropyl isostearate, stearic acid, isobutyl palmitate, isocetyl stearate, isopropyl laurate, hexyl laurate, decyl oleate, octadecan-2-ol, isocetyl alcohol, eicosanyl alcohol, behenyl alcohol, cetyl palmitate, silicone oils, such as dimethylpolysiloxne, di-n-butyl sebacate, isopropyl myristate, isopropyl palmitate, isopropyl stearate, butyl stearate, polyethylene glycol, lanolin, cacao butter, cottonseed oil, olive oil, palm oil, rapeseed oil, soybean oil, sunflower oil, avocado oil, almond oil, sesame oil, coconut oil, groundnut oil, castor oil, mineral oil, butyl myristate, isostearic acid, palmitic acid, isopropyl linoleate, lauryl lactate, decyl oleate or pyristyl myristate;

propellants, such as: propane, butane, isobutane, dimethyl ether, carbon dioxide or nitrogen dioxide;

solvents, such as: ethanol, methylene chloride, isopropanol, acetone, ethylene glycol monoethyl ether, diethylene glycol monobutyl ether, diethylene glycol monoethyl ether, dimethyl sulphoxide, dimethylformamide or tetrahydrofuran;

powders, such as chalk, talc, kaolin, starch, gums, colloidal silica, poly(sodium acrylate), tetraalkyl- and/or trialkylarylammonium smectites, chemically modified magnesium aluminosilicate, organically modified montmorillonite, hydrated aluminium silicate, pyrogenic silica, polycarboxyvinyl, sodium carboxymethylcellulose or ethylene glycol monostearate.

The compositions according to the invention generally comprise from 10 to 99% by weight of at least one vehicle as described above.

The compositions according to the invention are preferably provided in the form of emulsions, in which an oily component is present with an emulsifier, so as to form an oil-in-water or water-in-oil emulsion, depending on the value of the hydrophile/lipophile balance (HLB).

Thus, the compositions according to the invention can comprise one or more oily components or components having the properties of an oil.

It can relate to vegetable or mineral oils, such as those provided in the above list of emollients. It is also possible used volatile or non-volatile silicone oils, such as polydimethylsiloxanes.

These oily components can represent up to 90%, preferably from 10 to 80%, of the volume of the composition.

The compositions according to the invention can also comprise one or more emulsifiers. Depending on the nature of these emulsifiers, the compositions will be provided in the form of an oil-in-water or water-in-oil emulsion.

For the preparation of an emulsion of water-in-oil type, the emulsifier or emulsifiers chosen must exhibit a mean HLB of between 1 and 6. For the preparation of an emulsion of oil-in-water type, the emulsifier or emulsifiers chosen must exhibit a mean HLB greater than 6. The amount of these emulsifier in the compositions according to the invention can vary between 1 and 50% by weight, preferably between 2 and 20%.

These cosmetic compositions can also comprise surface-active agents which serve to disperse, emulsify, dissolve or stabilize various compounds used for their emollient or humectant properties. These surface-active agents are used in these compositions at concentrations varying from 0.05 to 50% by weight of the preparation. Anionic, non-ionic, cationic, zwitterionic or amphoteric surfactants or mixtures of these surfactants are thus found, such as:

Anionic Surfactants:

alkyl ester sulphonates of formula R—CH($SO_3$M)—COOR', where R represents a $C_8$–$C_{20}$, preferably $C_{10}$–$C_{16}$, alkyl radical, R' a $C_1$–$C_6$, preferably $C_1$–$C_3$, alkyl radical and M an alkali metal cation (sodium, potassium or lithium), substituted or unsubstituted ammonium (methyl-, dimethyl-, trimethyl- or tetramethylammonium, dimethylpiperidinium, and the like) or derivative of an alkanolamine (monoethanolamine, diethanolamine, triethanolamine and the like). Mention may very particularly be made of methyl ester sulphonates in which the R radical is $C_{14}$–$C_{16}$;

alkyl sulphates of formula ROSO$_3$M, where R represents a $C_{10}$–$C_{24}$, preferably $C_{12}$–$C_{20}$ and very particularly $C_{12}$–$C_{18}$ alkyl or hydroxyalkyl radical, M representing a hydrogen atom or a cation with the same definition as above, and their ethoxylated (EO) and/or propoxylated (PO) derivatives exhibiting, on average, from 0.5 to 6, preferably from 0.5 to 3, EO and/or PO units;

alkylamide sulphates of formula RCONHR'OSO$_3$M, where R represents a $C_2$–$C_{22}$, preferably $C_6$–$C_{20}$, alkyl radical and R' a $C_2$–$C_3$ alkyl radical, M representing a hydrogen atom or a cation with the same definition as above, and their ethoxylated (EO) and/or propoxylated (PO) derivatives exhibiting, on average, from 0.5 to 60 EO and/or PO units;

salts of saturated or unsaturated $C_8$–$C_{24}$, preferably $C_{14}$–$C_{20}$, fatty acids, $C_9$–$C_{20}$ alkylbenzenesulphonates, primary or secondary $C_8$–$C_{22}$ alkyl sulphonates, alkyl glycerol sulphonates, the sulphonated polycarboxylic acids described in GB-A-1,082,179, paraffin sulphonates, N-acyl-N-alkyltaurates, alkyl phosphates, alkyl isethionates, alkyl succinamates, alkyl sulphosuccinates, monoesters or diesters of sulphosuccinates, N-acylsarcosinates, sulphates of alkyl glycosides or polyethoxy-carboxylates, the cation being an alkali metal (sodium, potassium or lithium), a substituted or unsubstituted ammonium residue (methyl-, dimethyl-, trimethyl- or tetramethylammonium, dimethylpiperidinium, and the like) or derivative of an alkanolamine (monoethanolamine, diethanolamine, triethanolamine, and the like);

Non-Ionic Surface-Active Agents:

polyoxyalkylenated (polyethoxyethylenated, polyoxypropylenated or polyoxybutylenated) alkylphenols, the alkyl substituent of which is $C_6$–$C_{12}$, containing from 5 to 25 oxyalkylene units; mention may be made, by way of example, of Triton X-45, Triton X-114, Triton X-100 or Triton X-102 sold by Rohm & Haas Cy.;

glucosamides or glucamides;

glycerolamides derived from N-alkylamines (U.S. Pat. No. 5,223,179 and FR-A-1,585,966);

polyoxyalkylenated $C_8$–$C_{22}$ aliphatic alcohols containing from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Cy., or Kyro EOB, sold by The Procter & Gamble Cy.;

the products resulting from the condensation of ethylene oxide with a hydrophobic compound resulting from the condensation of propylene oxide with propylene glycol, such as the Pluronic sold by BASF;

amine oxides, such as ($C_{10}$–$C_{18}$ alkyl)-dimethylamine oxides or ($C_8$–$C_{22}$ alkoxy)-ethyldihydroxyethylamine oxides;

the alkyl polyglycosides described in U.S. Pat. No. 4,565, 647 and their polyoxyalkylenated [lacuna];

amides of $C_8$–$C_{20}$ fatty acids;

ethoxylated fatty acids;

ethoxylated amides, amines or amidoamines;

Amphoteric and Zwitterionic Surface-Active Agents:

alkyltrimethylsulphobetaines, condensation products of fatty acids and of protein hydrolysates, alkyl amphopropionates or -dipropionates, alkyl sultaines, or amphoteric derivatives of alkylpolyamines, such as Amphionic XL®, sold by Rhône-Poulenc, or Ampholac 7T/X® and Ampholac 7C/X®, sold by Berol Nobel, are used to decrease the irritation caused by other surface-active agents, mainly anionic surface-active agents.

Use may also be made of an emulsifier chosen from those on the following list:

| Chemical name of the emulsifier | Trade name | HLB |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Polyoxyethylene stearyl ether | Brij 72 | 4.9 |
| Polyoxyethylene sorbitol derivative of beeswax | G-1702 | 5 |
| Polyglyceryl-3 diisostearate | Plurol Diisostearic | 6 |
| PEG 200 dilaurate | Emerest 2622 | 6.3 |
| Sorbitan monopalmitate | Arlacel 40 | 6.7 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene monostearate | Myrj 45 | 11.1 |

-continued

| Chemical name of the emulsifier | Trade name | HLB |
|---|---|---|
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene 10 stearyl ether | Brij 76 | 12.4 |
| Polyoxyethylene 10 cetyl ether | Brij 56 | 12.9 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol derivative of lanolin | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene (20) sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene | Monostearate G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegoperse 4000 MS | 18.7 |

The compositions according to the invention can comprise water in a content which can range up to 80% by volume, preferably between 5 and 80%.

The compositions according to the invention can additionally comprise a high molecular weight silicone surface-active agent which can be an emulsifier used instead of those mentioned hereinabove.

This agent can be a high molecular weight dimethylpolysiloxane with polyoxyethylene and/or polyoxypropylene chains having a molecular weight of between 10,000 and 50,000 and with the structure:

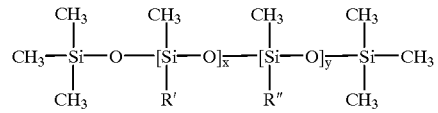

in which:
the R' and R" groups are chosen from H, $C_1$–$C_{18}$ alkyl and $[CH_2CH_2O]_a[CH_2CH(CH_3)O]_bH$; one of the R' and R" groups can be lauryl, the other having a molecular weight of between 1000 and 5000, a is between 9 and 115, preferably between 10 and 114, b is between 0 and 50, preferably between 0 and 49, x is between 133 and 673, preferably between 388 and 402, y is between 25 and 0.25, preferably between 15 and 0.75.

The dimethylpolysiloxane can be used in the form of a dispersion in a volatile siloxane, this dispersion comprising from 1 to 20% by volume of dimethylpolysiloxane.

The dimethylpolysiloxanes can be chosen from cyclomethicone and dimethicone copolyols, such as DC 3225C from Dow Corning, or lauryl methicone copolyol, such as DC Q2-5200 from Dow Corning.

It can also relate to Mirasil DMCO from Rhône-Poulenc or the cetyl dimethicone copolyol Abil AM90 from Th. Goldschmidt A G.

The composition according to the invention can comprise up to 25% by weight of such a surface-active agent.

The compositions according to the invention can also comprise an organic sunscreen, such as, for example:

| CTFA Name | Trade name | Sold by |
| --- | --- | --- |
| 3-Benzophenone | Uvinul M-40 | BASF |
| 4-Benzophenone | Uvinul MS-40 | BASF |
| 8-Benzophenone | Specra-Sorb UV-24 | American Cyanamid |
| Glyceryl PABA | Nipa GMPA | Nipa Labs |
| Octocrylene | Uvinul N-539 SG | BASF |
| Octyl dimethyl PABA | Escalol 507 | ISP |
| Octyl methoxycinnamate | Parsol MCX | Givaudan/Roux |
| Octyl salicylate | Uvinul O-18 | BASF |
| PABA | No. 102 | Merck |
| 2-Phenylbenzimidazole-5-sulphonic acid | Eusolex 232 | Merck |
| 3-(4-Methylbenzylidene) camphor | Eusolex 6300 | EM Ind. |
| 4-Isopropyldibenzoylmethane | Eusolex 8020 | EM Ind. |
| Butylmethoxydibenzoylmethane | Parsol 1789 | Givaudan/Roux |
| Etocrylene | Uvinul N-35 | BASF |

It is also possible to use, as sunscreen, any compound authorized in European Directive No. 76/768/EEC and its appendices.

The composition according to the invention can also comprise inorganic sunscreens, such as: zinc oxide in the form of particles with a mean size of between 1 and 300 nm, iron oxide in the form of particles with a mean size of between 1 and 300 nm and silica in the form of particles with a mean size of between 1 and 100 nm.

The compositions can also comprise additives, such as:
preservatives, for example para-hydroxybenzoate ester;
antioxidants, such as butylhydroxytoluene;
humectants, such as glycerol, sorbitol, dibutyl phthalate, gelatin or PEGs, for example PEGs 200–600;
buffer solutions, such as mixtures of lactic acid and of sodium hydroxide or of triethanolamine;
waxes, such as beeswax or paraffin wax;
plant extracts;
preservatives, such as the methyl, ethyl, propyl and butyl esters of p-hydroxybenzoic acid, sodium benzoate, Germaben (trade name) or any chemical agent which prevents bacterial proliferation or moulds and which is conventionally used of the cosmetic compositions, are generally introduced into these compositions at a level of 0.01 to 3% by weight. The amount of these products is generally adjusted in order to prevent any proliferation of bacteria, moulds or yeasts in the cosmetic compositions. As an alternative to these chemical agents, it is sometimes possible to use agents which modify the activity of the water and which greatly increase the osmotic pressure, such as carbohydrates or salts;
. . .

The cosmetic compositions forming the subject-matter of the invention can also comprise fixative resins. These fixative resins are generally present at concentrations of between 0.01 and 10% preferably between 0.5 and 5%. The constituent fixative resins of the cosmetic compositions forming the subject-matter of the invention are preferably chosen from the following resins: acrylate/acrylamide copolymer, poly (vinyl methyl ether)/maleic anhydride copolymer, vinyl acetate/crotonic acid copolymer, octylacrylamide/acrylate/butylaminoethyl methacrylate copolymer, polyvinylpyrrolidone (PVP), copolymers of polyvinylpyrrolidone and of methyl methacrylate, copolymer of polyvinylpyrrolidone and of vinyl acetate (VA), poly(vinyl alcohol), copolymer of poly(vinyl alcohol) and of crotonic acid, copolymer of poly(vinyl alcohol) and of maleic anhydride, hydroxypropyl cellulose, hydroypropyl guar, sodium polystyrenesulphonate, polyvinylpyrrolidone/ethyl methacrylate/methacrylic acid terpolymer, monomethyl ether of poly(methyl vinyl ether—maleic acid), poly (ethylene glycol terephthale)/poly(ethylene glycol) copolymers, poly(ethylene glycol terephthalate)/poly (ethylene glycol)/poly(sodium sulphoisophthalate) copolymers, and their mixtures. The fixative resins can also comprise grafted functionalized polyorganosiloxane units, as described in Patent WO 95/06079.

The fixative resins will preferably be of the following type: polyvinylpyrrolidone (PVP), copolymers of polyvinylpyrrolidone and of methyl methacrylate, copolymer of polyvinylpyrrolidone and of vinyl acetate (VA), poly (ethylene glycol terephthale)/poly(ethylene glycol) copolymers, poly(ethylene glycol terephthalate)/poly (ethylene glycol)/poly(sodium sulphoisophthalate) copolymers, and their mixtures.

These fixative resins are preferably dispersed or dissolved in the chosen vehicle.

The cosmetic compositions forming the subject-matter of the invention can also comprise polymeric derivatives exercising a protective function.

These polymeric derivatives can be present in amounts of the order of 0.01 to 10%, preferably approximately 0.1 to 5% and very particularly of the order of 0.2 to 3% by weight, agents such as cellulose derivatives, such as cellulose hydroxyethers, methylcellulose, ethylcellulose, hydroxypropyl methylcellulose or hydroxybutyl methylcellulose poly(vinyl ester)s grafted onto polyalkylene backbones, such as poly(vinyl acetate)s grafted onto polyoxyethylene backbones (EP-A-219,048)

poly(vinyl alcohol)s polyester copolymers based on ethylene terephthalate and/or propylene terephthalate and polyoxyethylene terephthalate units, with an ethylene terephthalate and/or propylene terephthalate (number of units)/polyoxyethylene terephthalate (number of units) molar ratio of the order of 1/10 to 10/1, preferably of the order of 1/1 to 9/1, the polyoxyethylene terephthalates exhibiting polyoxyethylene units having a molecular weight of the order of 300 to 5000, preferably of the order of 600 to 5000 (U.S. Pat. No. 3,959,230, U.S. Pat. No. 3,893,929, U.S. Pat. No. 4,116,896, U.S. Pat. No. 4,702,857 and U.S. Pat. No. 4,770,666);

sulphonated polyester oligomers obtained by sulphonation of an oligomer derived from from ethoxylated allyl alcohol, dimethyl terephthalate and 1,2-propylenediol exhibiting from 1 to 4 sulphonated groups (U.S. Pat. No. 4,968,451)

polyester copolymers based on propylene terephthalate and polyoxyethylene terephthalate units and terminated by ethyl or methyl units (U.S. Pat. No. 4,711,730) or polyester oligomers terminated by alkyl polyethoxy groups (U.S. Pat. No. 4,702,857) or anionic sulphopolyethoxy (U.S. Pat. No. 4,721,580) or anionic sulphoaroyl (U.S. Pat. No. 4,877,896) groups polyester polyurethanes obtained by reaction of a polyesters with a number [lacuna] molecular mass of 300–4000, obtained from adipic acid and/or from terepthalic acid and/or from sulphoisophthalic acid and from a diol with a mass of less than 300, with a prepolymer containing terminal isocyanate groups obtained from a polyoxyethylene glycol with a molecular mass of 600–4000 and from a diisocyanate (FR-A-2,334,698)

ethoxylated monoamines or polyamines or polymers of ethoxylated amines (U.S. Pat. No. 4,597,898 and EP-A-11,984)

sulphonated polyester oligomers obtained by condensation of isophthalic acid, of dimethyl sulphosuccinate and of diethylene glycol (FR-A-2,236,926).

The performances of the cosmetic compositions forming the subject-matter of the invention can also be improved by the use of plasticizers. The plasticizer can constitute between 0.1 and 20% of the formulation, preferably from 1 to 15%. Mention may be made, among particularly useful plasticizers, of adipates, phthalates, isophthalates, azelates, stearates, silicone copolyols, glycols, castor oil or their mixtures.

It is also advantageously possible to add, to these compositions, metal-sequestering agents, more particularly those sequestering calcium, such as citrate ions, or emollients, such as silicones or oils or fatty substances used in this connection in the cosmetics industry (mineral oils, fatty acid esters, triglycerides, silicones, and the like).

It is also possible to add water-soluble or water-dispersible polymers, such as collagen or certain non-allergizing derivatives of animal or plant proteins (wheat protein hydrolisates, for example), natural hydrocolloids (guar gum, locust bean gum, tara gum, and the like) or hydrocolloids resulting from fermentation processes, such as xanthan gum, and derivatives of these polycarbohydrates, such as modified celluloses (for example, hydroxyethylcellulose or carboxymethylcellulose), or guar or locust bean derivatives, such as their cationic derivatives or some non-ionic derivatives (for example, hydroxypropylguar) or the anionic derivatives (carboxymethylguar and carboxymethylhydroxypropylguar).

Inorganic powders or particles, such as calcium carbonate, inorganic oxides in the powder form or in the colloidal form (particles with a size of less than or of the order of a micrometer, sometimes of a few tens of nanometers), such as silica, aluminium salts generally used as antiperspirants, kaolin, talc, clays and their derivatives, and the like, can be added in combination to these compounds.

One or more fragrances, colouring agents, among which may be mentioned the products described in Appendix IV ("List of colouring agents allowed for use in cosmetic products") of European Directive No. 76/768/EEC of Jul. 27, 1976, known as the cosmetic directive, and/or opacifying agents, such as pigments, can generally be added to these ingredients to increase the attractiveness during use of the composition by the consumer.

Finally, the composition can also contain viscosifying or gelling polymers, such as crosslinked polyacrylates (Carbopol, sold by Goodrich), cellulose derivatives, such as hydroxypropylcellulose or carboxymethylcellulose, guars and their derivatives, locust bean, tara or cassia gum, xanthan gum, alginates, carrageenans, or chitin derivatives, such as chitosan, used alone or in combination, or the same compounds, generally in the form of water-soluble polymers modified by hydrophobic groups bonded covalently to the polymer skeleton, as described in Patent WO 92/16187, and/or water, in order to bring the total of the constituents of the formulation to 100%.

The cosmetic compositions forming the subject-matter of the invention can also comprise polymeric dispersing agents in an amount of the order of 0.1 to 7% by weight, in order to control the calcium and magnesium hardness, agents such as:

water-soluble salts of polycarboxylic acids with a molecular mass of the order of 2000 to 100,000, obtained by polymerization or copolymerization of ethylenically unsaturated carboxylic acids, such as acrylic acid, maleic acid or anhydride, fumaric acid, itaconic acid, aconitic acid, mesaconic acid, citraconic acid or methylenemalonic acid, and very particularly polyacrylates with a molecular mass of the order of 2000 to 10,000 (U.S. Pat. No. 3,308,067) or copolymers of arylic acid and of maleic anhydride with a molecular mass of the order of 5000 to 75,000 (EP-A-66,915)

poly(ethylene glycol)s with a molecular mass of the order of 1000 to 50,000.

The invention also relates to a coating composition comprising the particles according to the invention and at least one binder.

The coating compositions are preferably transparent, such as, for example, transparent covering or varnish compositions. Transparent coating is understood to mean a coating through which the treated substrate can be seen. It may or may not be coloured.

This coating composition can be based on an aqueous or organic solvent.

When the solvent is organic, it can be chosen from:

aliphatic hydrocarbons (white spirit type), is aromatic hydrocarbons (xylene type) or terpenic hydrocarbons (turpentine type), acetates (butyl acetate type), ketones (acetone type), alcohols (butanol type), or mixtures of these solvents.

The titanium dioxide particles, in the form of a dispersion or of a powder, exhibit the characteristics defined above.

The binder can be chosen from water-soluble polymers, latices of alkyd, aminoplast, acrylic or styrene/acrylic, vinyl, cellulose, polyurethane or epoxy type, and the like. These binders are as well suited to coating compositions in the aqueous phase as in the organic phase.

According to a preferred alternative form, it is possible to use acrylic latices of small size, i.e. with a size of less than 100 nm, such as Rhodopas Ultrafine® latices sold by Rhône-Poulenc, in particular in a transparent covering.

The composition can also comprise a surface-active agent.

The surface-active agent is preferably a non-ionic surface-active agent, for example an ethoxylated non-ionic surface-active agent with an ethoxylation number of between 3 and 12, for example a propoxylated (PO) surface-active agent. The amount of surface-active agent can be between 1 and 120% by weight with respect to the titanium dioxide, expressed on a dry basis.

This composition can comprise agents of any type conventionally used in the coating application, such as thickeners, biocidal agents, anti-UV agents (HALS or organic absorbers), colouring pigments or coalescence agents.

The content of titanium dioxide particles in the said composition is generally such that the content of titanium dioxide in the dry coating obtained from the composition is at most 10% by weight, preferably between 1 and 8%.

This composition can be used in particular for any transparent coating, in particular in a transparent covering or in a varnish.

They are particularly stable on storage and it may be observed that the titanium dioxide particles retains their dispersion index in the formulation.

The following examples illustrate the invention without, however, limiting the scope thereof.

EXAMPLES

Example 1

Preparation of a Dispersion 1 According to the Invention With a Treatment Based on $CeO_2$ and $SiO_2$ Stage 1—Hydrolysis The following are successively added to 394.7 g of a 1.9 mol/kg titanium oxychloride solution:

42.02 g of 36% hydrochloric acid, 4.73 g of citric acid, 547.1 g of purified water, 11.36 g (0.2% /$TiO_2$) of anatase seeds exhibiting a size of between 5 and 6 nm.

The mixture is brought to boiling point is is maintained there for 3 h.

Stage 2—Recovery of the Particles and Redispersing

The solution is subsequently filtered and the particles obtained are washed with water until the chlorides have been completely removed. They are subsequently redispersed at pH 9 (controlled by the addition of sodium hydroxide). The solids content is 20% by weight.

The dispersion obtained is stable. The size of the particles, measured by TEM, is 45 nm. X-ray diffraction analysis shows that the particles are based on titanium dioxide solely in the anatase form.

Their relative density is 2.5 (Vi=0.14 cc/g).

The specific surface, measured by the BET method on the particles of the dispersion which have been dried at a degassing temperature of 150° C., is 300 m$^2$/g.

Stage 3—Treatment of the Particles With a Cerium Compound

Use is made of a solution 1, which is an aqueous cerium acetate solution comprising 3.3% by weight of CeO2.

2822 g of the dispersion obtained on conclusion of Stage 2 are introduced into a reactor equipped with a stirrer. 5000 g of purified water are then added. The pH of the dispersion is adjusted to 9.1 by addition of sodium hydroxide. The temperature is maintained at 25° C.

456 g of the solution 1 are subsequently introduced continuously with a flow rate of 9.5 g/min. The pH is regulated at 9 by simultaneous introduction of a 10% aqueous sodium hydroxide solution.

A maturing is subsequently carried out for 15 min with stirring.

Stage 4—Treatment of the Particles With a Silicon Compound

Use is made of the solution 2, which is an aqueous sodium silicate solution comprising 26.2% by weight of SiO2.

The reaction mixture resulting from Stage 3 is heated to 90° C. (rise in temperature over 1 h 30 min) and the pH is regulated at 8.

381 g of the solution 2 are introduced with a flow rate of 6.3 g/min, the heating is then switched off and cooling is allowed to take place to room temperature.

125 ml of 3M $H_2SO_4$ are introduced, the pH is 5.5

The dispersion obtained is washed by ultrafiltration.

Results

The solids content of the dispersion is 25% by weight.

The size of the particles, measured by TEM, is 45 nm.

The level of cerium, measured by X-ray fluorescence, is 4.5% by weight, expressed as $CeO_2$, measured by X-ray fluorescence, with respect to the $TiO_2$, the level of $SiO_2$ is 30% by weight.

The specific surface, measured by the BET method on the particles of the dispersion which have been dried under vacuum at a temperature of 150° C. for 4 hours, is 100 m$^2$/g.

The relative density is 2.48.

The viscosity is 400 mPa·s.

The dispersion index is 0.4. This dispersion is particularly stable: after one month, the measurement of the dispersion index remains 0.4.

Example 2

Preparation of a Dispersion 2 According to the Invention With Surface Treatment Based on $CeO_2$, $SiO_2$ and $Al_2O_3$ Stage 1—Hydrolysis The following are successively added to 394.7 g of a 1.9 mol/kg titanium oxychloride solution:

42.02 g of 36% hydrochloric acid, 4.73 g of citric acid, 547.1 g of purified water, 5.68 g (0.1%/$TiO_2$) of anatase seeds exhibiting a size of between 5 and 6 nm.

The mixture is brought to boiling point is is maintained there for 3 h.

Stage 2—Recovery of the Particles and Redispersing

The solution is subsequently filtered and the particles obtained are washed with water until the chlorides have been completely removed. They are subsequently redispersed at pH 9 (controlled by the addition of sodium hydroxide) with a solids content is of 25% by weight.

The dispersion obtained is stable. The size of the particles, measured by TEM, is 60 nm. X-ray diffraction analysis shows that the particles are based on titanium dioxide solely in the anatase form.

Their relative density is 2.52 (Vi=0.14 cc/g).

The specific surface, measured by the BET method on the particles of the dispersion which have been dried at a degassing temperature of 150° C., is 300 m$^2$/g.

Stage 3—Treatment of the Particles With a Cerium Compound

Use is made of a solution 4, which is an aqueous cerium acetate solution obtained by dissolving 13.56 g of cerium acetate in 750 g of water.

1159 g of the dispersion obtained on conclusion of Stage 2 are introduced into a 3 liter reactor equipped with a stirrer. 240 g of purified water are then added. The pH of the dispersion is adjusted to 9 by addition of sodium hydroxide. The temperature is maintained at 25° C.

The solution 4 is subsequently introduced continuously with a flow rate of 500 ml/h. The pH is regulated at 9 by simultaneous introduction of a 5M aqueous sodium hydroxide solution and of a 1M aqueous phosphoric acid solution. A maturing is subsequently carried out for 1 hour at 25° C., still with stirring.

Stage 4—Treatment of the Particles With Silica and Alumina

The following solutions are used:

solution 2: aqueous cerium silicate solution obtained by dissolving 108.78 g of sodium silicate in 100 g of water (sodium silicate comprising 355 g/l of $SiO_2$ and $SiO_2$/$Na_2O$ molar ratio of 3.3).

solution 3: aqueous sodium aluminate solution obtained by dissolving 39.28 g of sodium aluminate in 40 g of water (sodium aluminate comprising 24% of $Al_2O_3$ and 19% of $Na_2O$).

The reaction mixture is subsequently heated to 90° C. (rise in temperature over 35 min) and the solution 2 is introduced with a flow rate of 2 ml/min. The pH is regulated at 9 by introduction of 3M $H_2SO_4$. A maturing time of 1 hour is carried out at 90° C.

The solution 3 is introduced, still at 90° C. and at pH 9, with a flow rate of 2 ml/min and then maturing is allowed to take place for 1 hour. The reaction mixture is subsequently cooled to room temperature.

Results

The dispersion obtained is centrifuged. The cake obtained is washed with purified water and then this cake is redispersed in aqueous medium at pH 9.

The solids content of the dispersion is 25% by weight.

The size of the particles, measured by TEM, is 60 nm. The level of cerium is 5% by weight, expressed as $Ce_2O$, with respect to the $TiO_2$, the level of $SiO_2$ is 15% by weight and that of $Al_2O_3$ is 5%.

The specific surface, measured by the BET method on the particles of the dispersion which have been dried under vacuum at a temperature of 150° C. for 4 hours, is 120 m²/g.

The relative density is 2.50.

The viscosity is 500 mPa·s.

The dispersion index is 0.4. This dispersion is particularly stable: after one month, the measurement of the dispersion index remains 0.4.

Example 3

Preparation of a Dispersion 3 According to the Invention With a Treatment Based on $CeO_2$, $SiO_2$ and $Al_2O_3$ Stages 1 and 2 of Example 1 are employed.

Stage 3—Treatment of the Particles With a Cerium Compound

Use is made of a solution 1, which is an aqueous cerium acetate solution obtained by dissolving 13.56 g of cerium acetate in 750 g of purified water. 1159 g of the dispersion obtained on conclusion of Stage 2 are introduced into a 3 liter reactor equipped with a stirrer. 240 g of purified water are then added. The pH of the dispersion is adjusted to 9 by addition of sodium hydroxide. The temperature is maintained at 25° C.

The solution 1 is subsequently introduced continuously with a flow rate of 2 ml/min. The pH is regulated at 9 by simultaneous introduction of a 5M aqueous sodium hydroxide solution and of a 1M aqueous phosphoric acid solution. A maturing is subsequently carried out for 1 hour at 25° C., still with stirring.

Stage 4—Treatment of the Particles With Silicon and Aluminium Compounds

The following solutions are used:

solution 2: aqueous sodium silicate solution obtained by dissolving 108.78 g of sodium silicate in 100 g of water (sodium silicate comprising 355 g/l of $SiO_2$ and $SiO_2$/$Na_2O$ molar ratio of 3.3)

solution 3: aqueous sodium aluminate solution obtained by dissolving 39.28 g of sodium aluminate in 40 g of water (sodium aluminate comprising 24% by weight of $Al_2O_3$ and 19% by weight of $Na_2O$).

The reaction mixture resulting from Stage 3 is heated to 90° C. (rise in temperature over 35 min) and the solution 2 is introduced with a flow rate of 2 ml/min. The pH is regulated at 9 by the introduction of 3M $H_2SO_4$. A maturing time of 1 hour is carried out at 90° C.

The solution 3 is introduced, still at 90° C. and at pH 9, with a flow rate of 2 ml/min and then maturing is allowed to take place for 1 hour. The reaction mixture is subsequently cooled to room temperature.

Results

The dispersion obtained is centrifuged. The cake obtained is washed with purified water and then this cake is redispersed in aqueous medium at pH 9.

The solids content of the dispersion is 25% by weight.

The size of the particles, measured by TEM, is 45 nm. The level of cerium is 5% by weight, expressed as $CeO_2$, with respect to the $TiO_2$, the level of $SiO_2$ is 15.75% by weight with respect to the $TiO_2$ and that of $Al_2O_3$ 5.25% with respect to the $TiO_2$.

The specific surface, measured by the BET method on the particles of the dispersion which have been dried under vacuum at a temperature of 150° C. for 4 hours, is 100 m²/g.

The relative density is 2.48.

The viscosity is 200 mPa·s.

The dispersion index is 0.4. This dispersion is particularly stable: after one month, the measurement of the dispersion index remains 0.4.

Example 4

Anti-UV Cosmetic Preparation

An anti-UV cosmetic composition according to the invention is prepared from the titanium dioxide dispersion of Example 3, the following formulation being followed:

| CTFA | Ingredients | % by weight |
|---|---|---|
| cyclomethicone and diphenyl dimethicone | Mirasil C-DPDM | 4 |
| caprylic capric trigiyceride | Miglyol 812 N | 4 |
| octyl palmitate | Crodamol OP | 4 |
| mineral oil | Marcol 82 | 5 |
| PVP/eicosene copolymer | Antaron V 220 | 3 |
| vitamin E acetate | | 0.3 |
| glyceryl stearate | | |
| propyleme glycol stearate | | |
| glyceryl isostearate | Hydrolactol 70 | 10 |
| propyleme glycol isostearate | | |
| olleth 25 | | |
| ceteth 25 | | |
| potassium cecyl phosphate | Amphisol K | 2 |
| polysorbate 20 | Tween 20 | 1 |
| preservative | Germaben II | 0.2 |
| allantoin | | 0.2 |
| xanthan gum | Rhodicare D | 0.2 |
| dispersion, Example 2 | | 15.6 (5% as |

-continued

| CTFA | Ingredients | % by weight |
|---|---|---|
| | TiO2) | |
| lactic acid | | q.s. pH = 6.5 |
| deionized water | | q.s. 100 |

Photostability Test

The cosmetic composition to be tested is introduced via a quartz cell into a Heraeus Sun-Test device and subjected to energy E of 500 W/m² at a temperature T of 30° C. for 1 h.

The photostability is monitored by visual observation of the colouring of the formulation. Visually, no blueing is observed.

Measurement of the in Vitro SPF (Sun Protection Factor) Number

This number was measured using an SPF290 optometry device according to the method described in "Cosmetics & Toiletries", Vol. 107, No. 10, p.119.

The SPF number is 20±2 for an application of 2 mg/cm².

Measurement of the Dispersion Index of the Titanium [lacuna] Particles in the Formulation The dispersion index is 0.45, that is to say identical to that of the dispersion of titanium dioxide particles before formulation.

Example 5

Evaluation of the Properties of the Transparent Coverings

Preparation of the Transparent Coverings from Dispersions of Titanium Dioxide Particles The following components are mixed:

407.9 g of water, 3.7 g of Thixole® 60, sold by Coatex, which is a thickener, 2 g of Clerol® TPE 714, sold by Bevaloid, which is an antifoaming agent, 20 g of Dowanol® dpnb, sold by Dow, which is a coalescence agent, 20 g of propylene glycol, which is a coalescence agent, 523 g of DS 913, sold by Rhône-Poulenc, which is a styrene/acrylic latex, 3.3 g of Proxel® gxl, which is a biocidal agent, 3.4 g of 30% NaOH.

Mixing is carried out using a Rayneri stirrer, and then 55.06 g of a dispersion to be tested are added thereto.

Measurement of the Transparency

A film of transparent covering with a wet thickness of 100 μm is drawn over a piece of Leneta cardboard (black and white background), giving a dry film with a thickness of 20 μm.

The transparency is evaluated using a Datacolor DC 3890 spectrophotometer in enclosed specular mode. The result is expressed in ΔL (difference between the L of the black background treated with the transparent covering and of an untreated black background). The lower this ΔL, the better the transparency.

L is the measurement of the reflection (light/dark shade) in the intrinsic coloration quantified by means of the chromaticity coordinates L, a and b, given in the CIE 1976 system (L, a, b) as defined by the Commission Internationale d'Eclairage [International Commission on Illumination] and listed in the Recueil des Normes Francaises (AFNOR), colorimetric colour No. X08-12 (1983).

Measurement of the Anti-UV Activity

Three layers of transparent covering are applied in the proportion of 300 g/m² on wood panels (maritime pine, 15×18×1 cm³). These panels are exposed to UV radiation in a QUVB accelerated ageing device, sold by the company Q-Panel, operating at 60° C.

The anti-UV protection can be evaluated both by visual assessment and a calorimetric measurement through the change in the reflection factor L as defined above. This is because, during the accelerated ageing, the greater the fall in L, the more the wood dulls and ages.

The result was expressed in ΔL, which is the difference between the starting L of the wood and the L of the wood after accelerated ageing.

It is observed, for the transparent covering not comprising titanium dioxide particles, exhibits a ΔL of 12; the colour after ageing is very heterogeneous (flaking).

Measurement of the Photocatalytic Activity

The photocatalytic activity is evaluated on the titanium dioxide particles in the form of a powder. For this, the titanium dioxide dispersions are dried in an oven at 120° C.

The test consists in measuring the rate of photooxidation of the gas isopropanol by titanium dioxide according to a test with the same principle as that described in the article by Irick G., Strickland T. H. and Zanucci J. S., Permanence of Organic Coatings, ASTM STP 781, 1982, p. 35–42.

3 ml of isopropanol and 1.5 g of titanium dioxide to be tested are introduced into a Pyrex tube. The titanium dioxide is immobilized in the form of a pellet on a metal support; the titanium dioxide surface exposed to the UV radiation is 10 cm². The tube is subsequently sealed.

The test apparatus is composed of a turntable rotating about 3 low-pressure UVA lamps exhibiting an emission maximum between 300 and 400 nm. The tube comprising the sample is placed in the turntable, the face of the support comprising the titanium dioxide to be evaluated towards the UVA radiation. The turntable is itself placed in an oven at 60° C.

The luminous power in the UVA received by the titanium dioxide is approximately 30 W/m².

The isopropanol in the vapour phase is adsorbed on the titanium dioxide and reacts with the oxygen to form acetone.

The progress of the photodecomposition of the isopropanol is quantitatively determined regularly over a period of 24 hours, using a gas chromatograph, by monitoring the amount of $O_2$ remaining in the tube. This progress is expressed using the rate constant for disappearance of the $O_2$, expressed in mmol/h/m².

The higher the rate of photooxidation measured by this test, the greater the deterioration in the transparent covering.

The results of this test were confirmed by an evaluation of the visual appearance of the transparent covering after 200 cycles of accelerated ageing as described above. According to the photocatalytic activity, a more or less pronounced chalking may be observed.

The dispersion 3 is tested, as well as a dispersion 4 of the prior art which is a dispersion of rutile titanium dioxide particles exhibiting a solids content of 25% by weight. The particles of this dispersion 4 exhibit a mean size of 80 nm and a surface treatment based on silica in a content of 110% by weight.

| | Results | | | | |
|---|---|---|---|---|---|
| | | | Photocatalytic activity | | |
| | | Anti-UV | Rate | Appearance of the film | |
| Dispersion | Transparency ΔL | activity: ΔL after 20 cycles | disappearance $O_2$ (mmol/h/m$^2$) | in the initial state | after 200 cycles |
| Dispersion 3 | 4.3 | 6 | 0.23 | homogeneous | a small amount of chalking |
| Dispersion 4 (prior art) | 5.7 | 8 | 0.33 | heterogeneous | chalking |

It is observed that the dispersions of particles of titanium dioxide treated with cerium exhibit a low photocatalytic activity. This makes it possible to avoid the chalking of the transparent covering and to preserve, in this transparent covering, its initial appearance while providing an anti-UV protection.

Furthermore, these transparent coverings exhibit a good transparency.

What is claimed is:

1. Anatase titanium dioxide particles with a size of at most 100 nm, wherein said particles are at least partially covered:
   with a first layer of at least one cerium and/or iron compound, and
   with a second layer of at least one metal oxide, hydroxide or hydroxide oxide,
   and wherein these particles exhibit a BET specific surface of at least 70 m$^2$/g and a relative density of the order of 2.5.

2. Particles according to claim 1, wherein the first layer is based on at least one cerium compound in a content such that the ratio of the cerium compound to the titanium dioxide particles is at most 6% by weight.

3. Particles according to claim 1, wherein the second layer is based on silica and/or on an aluminium hydroxide or hydroxide oxide, in the simple or mixed form.

4. Particles according to claim 3, wherein the first layer is based on a layer of silica is a content by weight of 30% of $SiO_2$ with respect to the titanium dioxide particles.

5. Particles according to claim 1, which are provided in the form of a dispersion.

6. Particles according to claim 5, wherein the dispersion index in the liquid phase is at most 0.5.

7. Particles according to claim 5, wherein the liquid phase of the dispersion is aqueous.

8. Particles according to claim 7, wherein the dispersion exhibits a conductivity of at most 3 msiemens.

9. Particles according to claim 7, wherein the solids content of the dispersion is at least 35% by weight and the viscosity of said dispersion is at most 1000 mPa·s.

10. Particles according to claim 5, wherein the liquid phase of the dispersion is organic.

11. Particles according to claim 10, wherein the organic dispersion is obtained by mixing particles in an aqueous dispersion with an organic medium comprising a transfer agent, the latter being chosen from quaternary amines or quaternary ammonium salts.

12. Particles according to claim 1, which are agglomerated and are provided in the form of a powder.

13. Process for the preparation of particles according to claim 1, wherein the following stages are employed:
   at least one cerium and/or iron compound is precipitated at the surface of anatase titanium dioxide particles with a size of at most 100 nm, the particles exhibiting a BET specific surface of at least 200 m$^2$/g and a relative density of the order of 2.5, then
   at least one metal oxide, hydroxide or hydroxide oxide is precipitated at the surface of particles obtained.

14. Preparation process according to claim 13, wherein the starting titanium dioxide particles are obtained by hydrolysis of at least one titanium compound A in the presence of at least one compound B comprising:
   (i) acids which exhibit:
      either a carboxyl group and at least two hydroxyl and/or amine groups,
      or at least two carboxyl groups and at least one hydroxyl and/or amine group,
   (ii) organic phosphoric acids of following formulae:

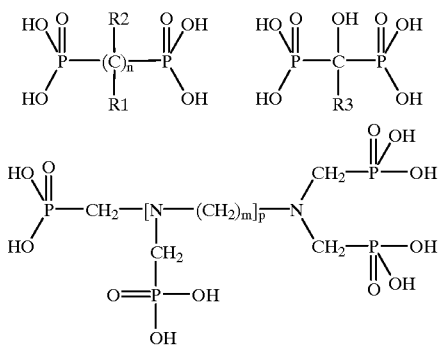

in which n and m are integers of between 1 and 6 and p is an integer of between 0 and 5; R1, R2 and R3, which are identical or different, representing a hydroxyl, amino, aralkyl, aryl or alkyl group or hydrogen,
   (iii) compounds capable of releasing sulphate ions in acidic medium,
   (iv) salts of the acids described above,
   and in the presence of anatase titanium dioxide seeds exhibiting a size of at most 8 nm and a weight ratio expressed as $TiO_2$ present in the seeds/titanium present before introduction of the seeds in the hydrolysis medium, expressed as $TiO_2$, of between 0.01% and 3%.

15. Process according to claim 14, wherein the titanium compound A is titanium oxychloride.

16. Process according to claim 14, wherein the compound B is citric acid.

17. Anti-UV cosmetic composition comprising titanium dioxide particles according to claim 1, in an amount such that the content of titanium dioxide in said composition is at least 1% by weight.

18. Anti-UV coating composition comprising at least one binder and titanium dioxide particles according to claim 1, in an amount such that the content of titanium dioxide in said composition is at most 10% by weight.

19. Anti-UV coating composition according to claim 18, further comprising a surface-active agent comprising an ethoxylated non-ionic surface-active agent exhibiting an ethoxylation number of between 3 and 12.

20. A method for preventing or treating damage by ultraviolet light, said method comprising applying an effective amount of a formulation containing the titanium dioxide particles according to claim 1 to an individual in need of such prevention or treatment.

* * * * *